United States Patent [19]
De Wet

[11] Patent Number: 5,985,291
[45] Date of Patent: *Nov. 16, 1999

[54] METHOD OF TREATING INFECTIONS USING MUPIROCIN CHLORHEXIDENE

[76] Inventor: Pieter M De Wet, Corporate Intellectual Property -U.S., UW2220, P.O. Box 1539, King of Prussia, Pa. 19406-0939

[ * ] Notice: This patent issued on a continued prosecution application filed under 37 CFR 1.53(d), and is subject to the twenty year patent term provisions of 35 U.S.C. 154(a)(2).

[21] Appl. No.: 08/977,934

[22] Filed: Nov. 24, 1997

Related U.S. Application Data

[63] Continuation of application No. 08/542,093, Oct. 12, 1995, abandoned.

[30] Foreign Application Priority Data

Apr. 18, 1995 [GB] United Kingdom .................... 9507825

[51] Int. Cl.$^6$ .................................................... A01N 25/34
[52] U.S. Cl. ......................... 424/400; 424/404; 424/445; 424/446; 424/447; 424/449; 514/723
[58] Field of Search ..................... 424/404, 445, 424/447, 446, 449; 514/171, 404, 451, 723

[56] References Cited

U.S. PATENT DOCUMENTS

| | | | |
|---|---|---|---|
| 4,122,158 | 10/1978 | Schmitt | 424/27 |
| 4,790,989 | 12/1988 | Hunter et al. | 424/404 |
| 4,879,287 | 11/1989 | Orr et al. | 514/171 |
| 5,098,417 | 3/1992 | Yamazaki et al. | 604/304 |

FOREIGN PATENT DOCUMENTS

| | | |
|---|---|---|
| 0095897 A2 | 12/1983 | European Pat. Off. . |
| 0128338 A1 | 12/1984 | European Pat. Off. . |
| 0167856 A2 | 1/1986 | European Pat. Off. . |
| 0251434 A2 | 1/1988 | European Pat. Off. . |

OTHER PUBLICATIONS

Lawrence, et al., "Preliminary Studies of the Use of Mupirocin in the Treatment of Burns", *Royal Society of Medicine*, 1984, pp. 165–172.

*Primary Examiner*—S. Mark Clardy
*Assistant Examiner*—Kathryne E. Shelborne
*Attorney, Agent, or Firm*—Elizabeth J. Hecht; Stuart R. Suter; William T. King

[57] ABSTRACT

A method of treating topical anti-bacterial infections which comprises the separate, simultaneous or sequential administration to a patient in need thereof an effective amount of mupirocin or a salt thereof and chlorhexidine or a salt thereof.

10 Claims, No Drawings

METHOD OF TREATING INFECTIONS USING MUPIROCIN CHLORHEXIDENE

This is a file wrapper continuation of application Ser. No. 08/542,093, filed Oct. 12, 1995 now abandoned.

This invention relates to novel method of treating topical bacterial infections using a combination of anti-bacterial agents.

Mupirocin, formerly known as pseudomonic acid, is a therapeutically useful compound which when active exhibits good antibacterial activity, mainly against Gram-positive bacteria, but also against some Gram-negative bacteria such as *Haemophilus influenzae* and *Moraxella catarrhalis*. It acts as selective reversible inhibitor of bacterial iso-leucyl t-RNA synthetase, thereby inhibiting bacterial protein synthesis. It also has anti-mycoplasma and anti-fungal activity (see Merck Index, 11th edn, 1989, 993 and references therein). The compound has an ester moiety which is susceptible to metabolism, effectively excluding the systemic use of the compound. It is however clinically effective as a topical agent. Topical antibacterial compositions comprising mupirocin are marketed in the UK by Beecham Research Laboratories under the trade names Bactroban Ointment and Bactroban Nasal. The first product is an ointment comprising a water soluble polyethylene glycol base (see also EP 0 095 897-A, Beecham Group) whilst the second product comprises the calcium salt of mupirocin in a white soft paraffin based ointment containing a glycerin ester (see also EP 0 167 856-A, Beecham Group). More recently, topical creams comprising mupirocin or a salt thereof have been described (W.O. 95110999, SmithKline Beecham). Further compositions, for use in treating fungal infections, are disclosed in EP-A-0 251 434 (Beecham Group), in particular, various cream formulations comprising liquid paraffin, water and an emulsifier. Such earlier patent applications refer generically to possible inclusion in compositions containing mupirocin of an additional therapeutic agent such as an antibacterial or antifungal agent, with specific reference to chlortetracycline and miconazole. In addition, EP 0 167 856-A (Beecham Group) discloses solutions of the calcium salt adapted for topical application to the eye and also optionally comprising chlorhexidine as a preservative.

Chlorhexidine is a bis-biguanide compound. It is an antibacterial agent active against both Gram-positive and Gram-negative bacteria, although less effective against some species of Pseudomonas (see Merck Index, 11th edn, 1989, 39 and 323 and references therein and The Pharmaceutical Codex, The Pharmaceuticals Press, 1994, 579). Chlorhexidine in particular is widely used in topical products, both as an anti-bacterial agent in its own right and also as a preservative.

The treatment of burns often requires the the concomitant use of an antibacterial agent as most burns tend to acquire a variety of pathogenic bacteria. The possible use of mupirocin in treating burns wounds has been previously investigated. Thus, Lawrence has shown that mupirocin was a very effective means of eliminating *Staph aureus* and *Staph pyogenes* from burns wounds but was not suitable for eliminating Gram negative bacteria such as *Pseud aeruginosa*. He further suggested that this deficiency could be overcome by providng a cream containing both mupirocin and an anti-bacterial agent effective against Gram negative bacteria and suggested phenoxetol as a suitable candidate (Mupirocin: a novel topical antibiotic; ed Wilkinson and Price, The Royal Society of Medicine, 1984, 163–171). It has also been suggested that this deficiency in activity may be overcome by the use of the silver salt of mupirocin (EP 0 128 338-A, Beecham Group). Chlorhexidine is also used in the treatment of burns, often as a component of a prophylactic product, in combination with other agents such as silver nitrate or phenoxetol.

There still remains the need for a superior method of treating topical bacterial infections which harnesses the anti-bacterial profile of mupirocin supplemented by the use of a secondary anti-bacterial agent, preferably as a synergistic combination.

Accordingly, the present invention provides a method of treating topical anti-bacterial infections which method comprises the separate, simultaneous or sequential administration to a patient in need thereof an effective amount of mupirocin or a salt thereof and chlorhexidine or a salt thereof.

The combination of mupirocin and chlorhexidine provides an antibacterial regime which has a broader spectrum of activity than either agent alone. In particular, the combination has superior activty against *Pseudomonas* sp than either agent alone.

Preferably, the method is used for treating infected burns injuries. The method may also be used for the prophylatic treatment of burns injuries.

Suitable salts of mupirocin include alkali metal and alkaline earth metal salts, for instance the sodium, lithium and calcium salts, as well as ammonium salts, substituted ammonium salts and the silver salt. A preferred salt is the crystalline calcium salt described in EP 0 167 856-A (Beecham Group), in particular the hydrate thereof which has from 1.8 to 2.2 moles, normally from 1.9 to 2.1 moles, of water per mole.

Suitable chlorhexidine salts are pharmaceutically acceptable and include the water soluble dihydrochloride, diacetate and digluconate salts.

Suitably, mupirocin and chlorhexidine are administered in a ratio of from about 10:1 to about 1:10 more suitably about 5:1 to 1:5, typically about 2:1 w/w, expressed as the weight of the free acid and free base respectively. Typically, equal volumes of topical mupirocin (2%) and chlorhexidine (1%) formulations are used.

Suitably, the administration is substantially simultaneous. This may conveniently be achieved by the co-administration of separate compositions comprising mupirocin or a salt thereof and chlorhexidine or a salt thereof. Such separate compositions may be usefully provided as a kit comprising a mupirocin formulation and a chlorhexidine formulation. Preferably in such kit, the formulations are provided in the relative amounts of 2:1, suitably as formulations comprising respectively mupirocin (2%) and chlorhexidine (1%), so that equal volumes of each may be dispensed.

Suitable topical compositions comprising mupirocin (2%, expressed as free acid) are marketed by SmithKline Beecham as Bactroban ointment and Bactroban Nasal, as hereinbefore described. In addition, the cream formulation described in PCT application number US94/12026 (SmithKline Beecham) may be used, if a more cosmetically acceptable product is required.

Suitable topical formulations comprising chlorhexidine are well known in the art and are readily available commercially.

The invention will now be described by the following examples which are illustrative and not intended to limit the invention hereinbefore described.

Example 1

Mupirocin Ointment

|  | % by wt |
|---|---|
| Mupirocin | 2 |
| Polyethylene glycol 400 | 59 |
| Polyethylene glycol 4000 | 39 |

Biological Data—in vitro Testing

The activity of topical formulations comprising mupirocin and chlorhexidine separately and a mixture the two formulations against a range of clinical isolates taken from infected burns wounds was evaluated using the Nathan agar-well diffusion assay.

The isolated organism, at a concentration of $10^5$ was used to seed the surface of a Meuller-Hinton sensitivity agar plate (4 mm) which would support the growth of the organism. A well (6 mm diam) was cut into the agar plate and filled with 12–15 mg of the test formulation. The plates were then incubated at 37° C. for 18 h and the size of the zone of inhibition recorded. A clear zone around a test well following the incubation period indicates that the formulation is active against the bacteria of the isolate being evaluated. The diameter of the zone of inhibition provides a measure of the relative potency of the formulation. For the purposes of this study, the following definitions were used:

| diameter of zone less than 10 mm | resistant |
|---|---|
| diameter of zone 10–20 mm | susceptible |
| diameter of zone greater than 20 mm | significantly susceptible |

The burn wound clinical isolates evaluated consisted of 57 Gram-negative and 43 Gram-positive bacteria.

The results are given in the following table:

| Formulation | zone < 10 mm | zone 10–20 mm | zone > 20 mm |
|---|---|---|---|
| mupirocin (2%) ointment* | 17 | 28 | 55 |
| chlorhexidine (1%) cream | 2 | 98 | 0 |
| mupirocin ointment and chlorhexidine** | 0 | 59 | 41 |

*see example 1
**1:1 by volume, effectively mupirocin (1%) and chlorhexine (0.5%)

Mupirocin ointment was found to be resistant to 17 of the 22 Pseudomonas aeruginosa isolates tested but active against all the Gram-positive and the remaining Gram-negative bacteria in the isolates examined. Chlorhexidine was ineffective against two *Streptococcus faecalis* organisms isolated from two different patients. The 50:50 combination of the two was however effective against all 100 bacterial isolates.

I claim:

1. A method of treating topical bacterial infections, which method comprises the administration to a patient in need thereof a topical pharmaceutical formulation containing an anti-bacterial amount of mupirocin or a salt thereof and chlorhexidine or a salt thereof.

2. The method according to claim 1 for treating infected burn injuries.

3. The method according to claim 1 for the prophylactic treatment of burn injuries.

4. The method according to claim 1, wherein the mupirocin and chlorhexidine are administered in a ratio of from about 10:1 to about 1:10 (w/w).

5. The method according to claim 1, wherein the mupirocin and chlorhexidine are administered in a ratio of from about 5:1 to about 1:5 (w/w).

6. The method according to claim 1, wherein the mupirocin and chlorhexidine are administered in a ratio of about 2:1 (w/w).

7. The method according to claim 1, wherein the formulation contains 2% mupirocin and 1% chlorhexidine.

8. A method of treating topical bacterial infections, which method comprises the administration to a patient in need thereof a formulation of a combination of mupirocin or a salt thereof and chlorhexidine or a salt thereof, in a ratio of from about 10:1 to about 1:10 (w/w).

9. A method of treating topical bacterial infections, which method comprises the simultaneous administration to a patient in need thereof of separate compositions of mupirocin or a salt thereof and chlorhexidine or a salt thereof, in a ratio of from about 10:1 to about 1:10 (w/w).

10. The method according to claim 9, wherein the mupirocin and chlorhexidine are administered in a ratio of about 2:1 (w/w).

* * * * *